United States Patent
Chang

(10) Patent No.: US 7,581,718 B1
(45) Date of Patent: Sep. 1, 2009

(54) ATOMIZER

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 0 days.

(21) Appl. No.: 12/103,828

(22) Filed: Apr. 16, 2008

(51) Int. Cl.
*B01F 3/04* (2006.01)

(52) U.S. Cl. ............ 261/78.2; 128/200.18; 128/200.21; 239/338

(58) Field of Classification Search ................ 261/78.1, 261/78.2, DIG. 55, DIG. 65; 128/200.18, 128/200.21, 200.22; 239/338
See application file for complete search history.

(56) References Cited

U.S. PATENT DOCUMENTS

| | | | |
|---|---|---|---|
| 2,772,117 A * | 11/1956 | Ritzau et al. | 239/135 |
| 5,054,477 A * | 10/1991 | Terada et al. | 128/200.14 |
| 5,409,170 A * | 4/1995 | Burwell et al. | 239/515 |
| 5,533,497 A * | 7/1996 | Ryder | 128/200.21 |
| 5,584,285 A * | 12/1996 | Salter et al. | 128/200.21 |
| 5,687,912 A * | 11/1997 | Denyer | 239/343 |
| 6,338,443 B1 * | 1/2002 | Piper | 239/340 |
| 6,796,513 B2 * | 9/2004 | Fraccaroli | 239/338 |
| 2002/0157663 A1 * | 10/2002 | Blacker et al. | 128/200.21 |
| 2003/0197068 A1 * | 10/2003 | Abate | 239/338 |
| 2005/0205085 A1 * | 9/2005 | Blacker et al. | 128/200.21 |

FOREIGN PATENT DOCUMENTS

| | | | | |
|---|---|---|---|---|
| EP | 170715 A1 * | 2/1986 | | 128/200.18 |
| EP | 587380 A1 * | 3/1994 | | 239/338 |

* cited by examiner

*Primary Examiner*—Richard L Chiesa
(74) *Attorney, Agent, or Firm*—Darby & Darby P.C.

(57) ABSTRACT

An atomizer includes: an enclosed reservoir defining an inner space adapted to receive a liquid therein; a jet nozzle provided in the inner space for passage of an air jet therethrough and formed with an air outlet; a jacket sleeved around the jet nozzle to define a fluid-introducing gap therebetween, the fluid-introducing gap being in fluid communication with the inner space; an air inlet conduit extending into the inner space, disposed above and connected to the jacket, and including a bottom wall having a jet-blocking portion aligned with the air outlet of the jet nozzle in a jet-ejecting direction, and a plurality of through-holes disposed around the jet-blocking portion and opening in the jet-ejecting direction; and a mist-discharging conduit extending sealingly into and in fluid communication with the inner space.

7 Claims, 5 Drawing Sheets

US 7,581,718 B1

ATOMIZER

BACKGROUND OF THE INVENTION

1. Field of the Invention

This invention relates to an atomizer, more particularly to an atomizer including an air inlet conduit for accelerating discharging of mist.

2. Description of the Related Art

An atomizer is a device for aerosolizing a liquid with a pressurized air, and has been used in the medical industry for delivering medicines to a patient's lungs.

In order to achieve highly efficient delivery of medicines, an air inlet conduit has been incorporated into the design of the atomizer. FIGS. 1 and 2 show conventional atomizers provided with the air inlet conduit. As shown in FIG. 1, an air inlet conduit 21 of the conventional atomizer 2 is used to introduce external air into an inner space 22 of the atomizer 2. The introduced air accelerates the aerosolizing mist of a drug to flow toward a mist-discharging conduit 23. Since the flow path of the introduced air is tortuous, the efficiency for delivery of the drug from the conventional atomizer to the patient is unsatisfactory.

As shown in FIG. 2, the conventional atomizer 3 includes an air inlet conduit 31 formed with a plurality of holes 311 in a peripheral wall thereof. Although the pathway of the introduced air into the inner space 32 is straight, the introduced air passing through the holes 311 formed in the peripheral wall cannot efficiently accelerate the mist to flow to a mist-discharging conduit due to a relatively long distance from the holes 311 to a mist forming zone $S_1$. The mist is also likely to flow into the air inlet conduit 31, thereby resulting in an unstable output. In addition, in the conventional atomizer 3, since a cap 33 and a jacket 34 are two individual parts, costs for manufacturing the atomizer 3 are increased, and the manufacturing process is relatively complicated. Moreover, since the jacket 34 is relatively small in size, it is likely to be misplaced.

Therefore, there is a need in the art to provide an atomizer that provides a high efficiency for delivery of a drug to a patient's lungs.

SUMMARY OF THE INVENTION

Therefore, an object of the present invention is to provide an atomizer that can overcome the aforesaid drawbacks of the prior art.

According to this invention, an atomizer includes: an enclosed reservoir defining an inner space adapted to receive a liquid therein; a jet nozzle provided in the inner space for passage of an air jet therethrough and formed with an air outlet; a jacket sleeved around the jet nozzle to define a fluid-introducing gap therebetween, the fluid-introducing gap being in fluid communication with the inner space for passage of the liquid therethrough; an air inlet conduit extending into the inner space, disposed above and connected to the jacket, and including a bottom wall having a jet-blocking portion aligned with the air outlet of the jet nozzle in a jet-ejecting direction so as to permit impingement of the air jet from the air outlet of the jet nozzle, and a plurality of through-holes disposed around the jet-blocking portion and opening in the jet-ejecting direction; and a mist-discharging conduit extending sealingly into and in fluid communication with the inner space for passage of a mist therethrough.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
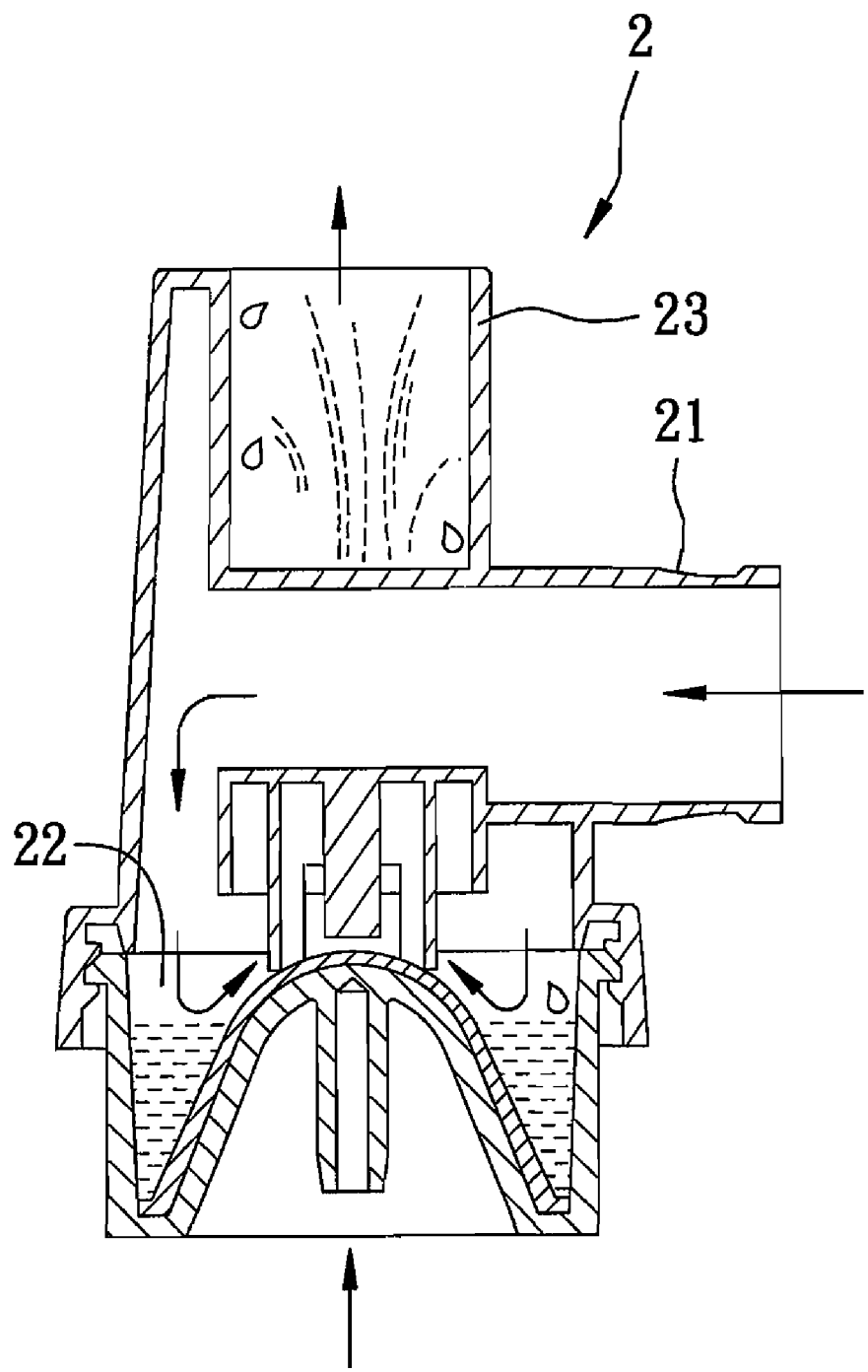
FIG. 1 is a cross-sectional view of a conventional atomizer.
Figure 2:
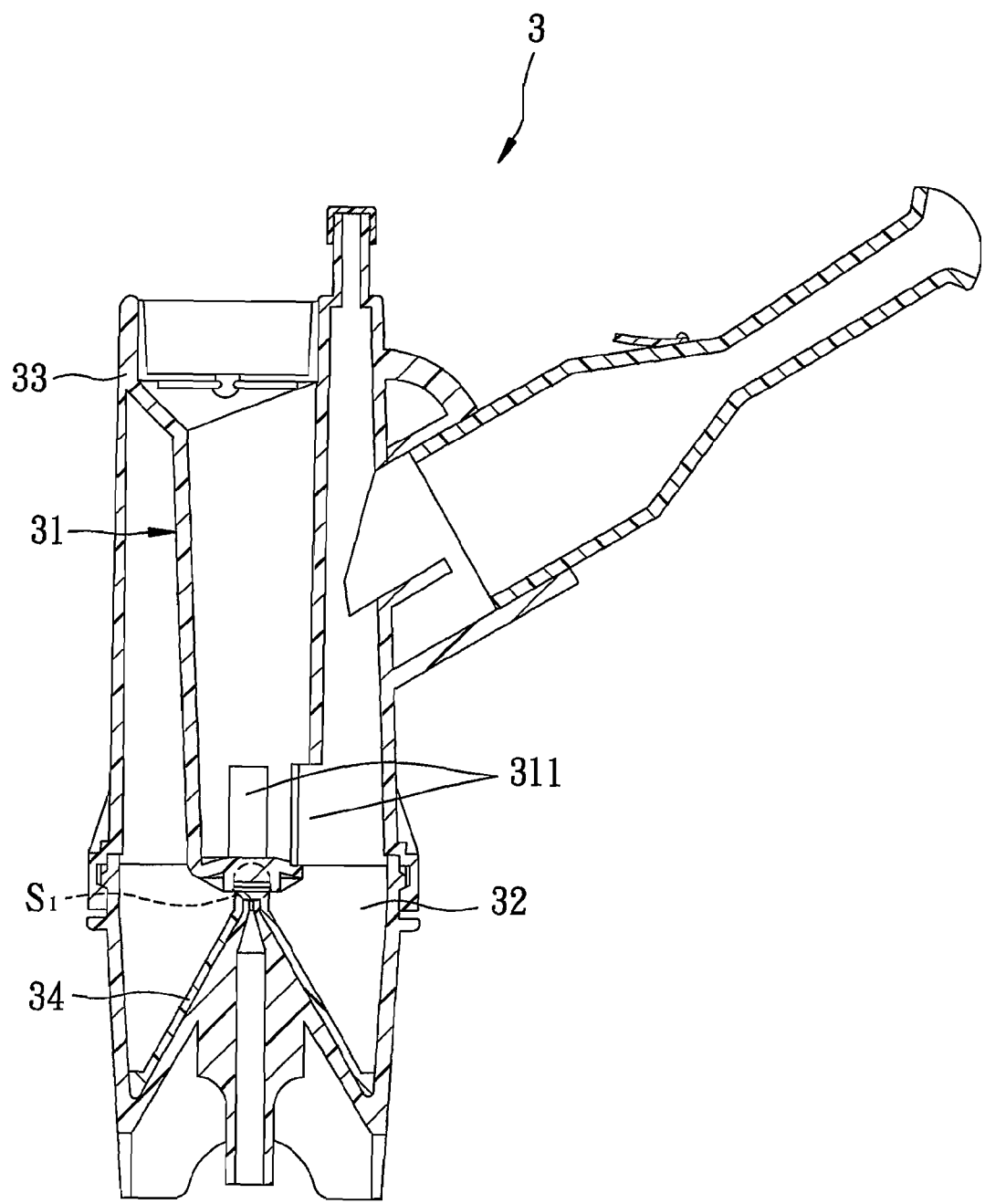
FIG. 2 is a cross-sectional view of another conventional atomizer.
Figure 3:
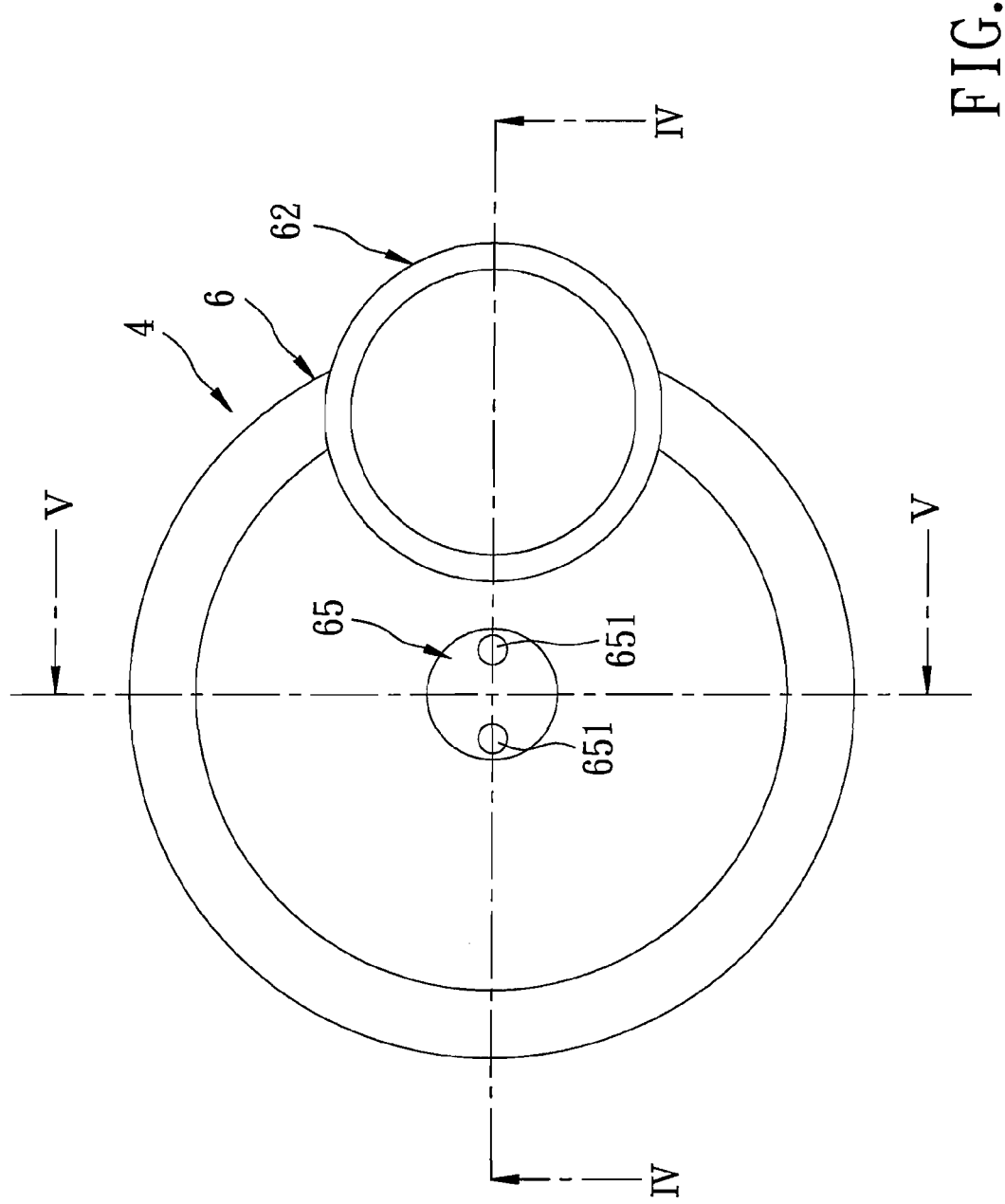
FIG. 3 is a schematic view of the preferred embodiment of an atomizer according to this invention, illustrating the position relationship between through-holes of an air inlet conduit and a mist-discharging conduit.
Figure 4:
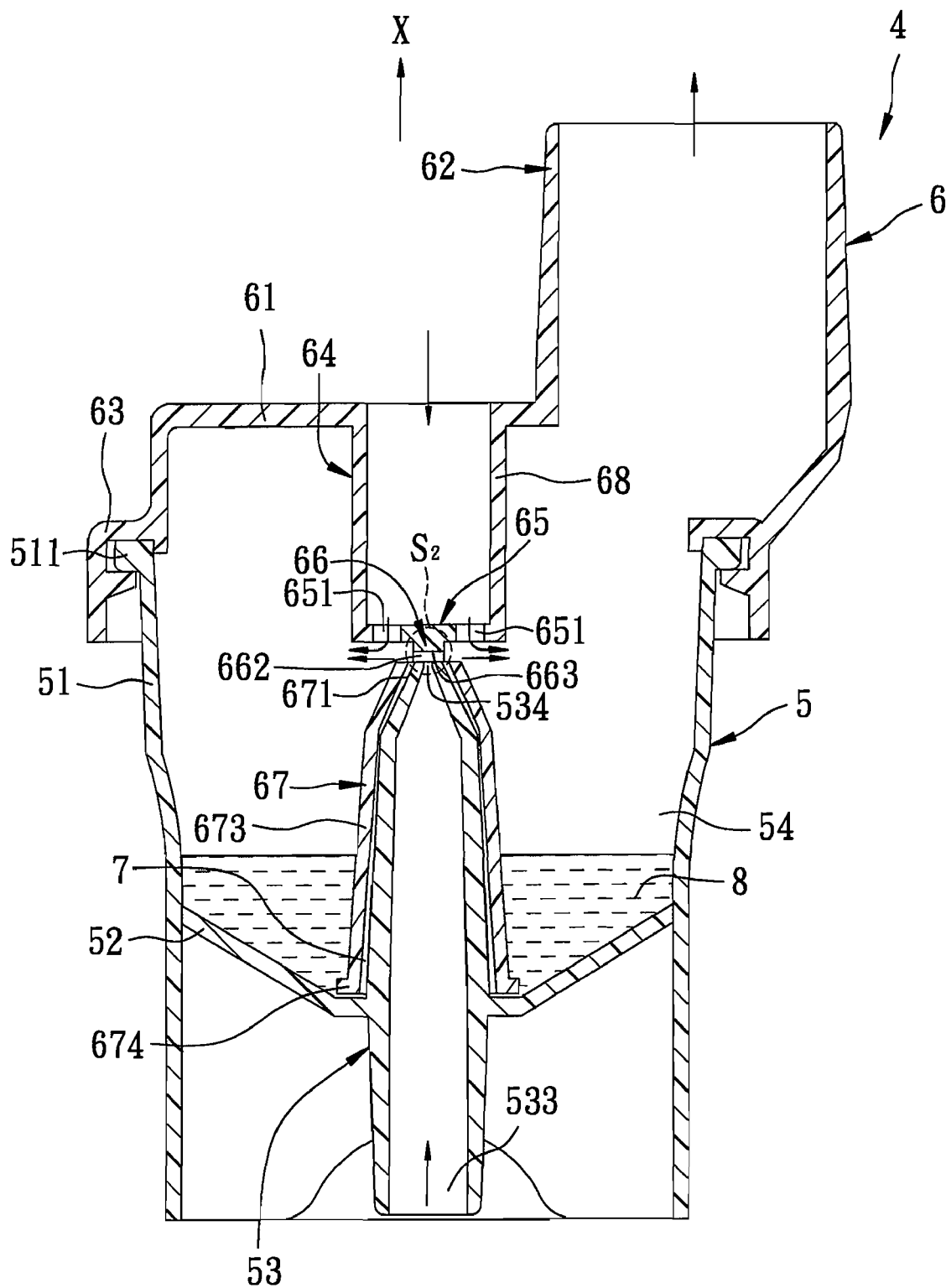
FIG. 4 is a cross-sectional view of the preferred embodiment taken along line IV-IV in FIG. 3.
Figure 5:
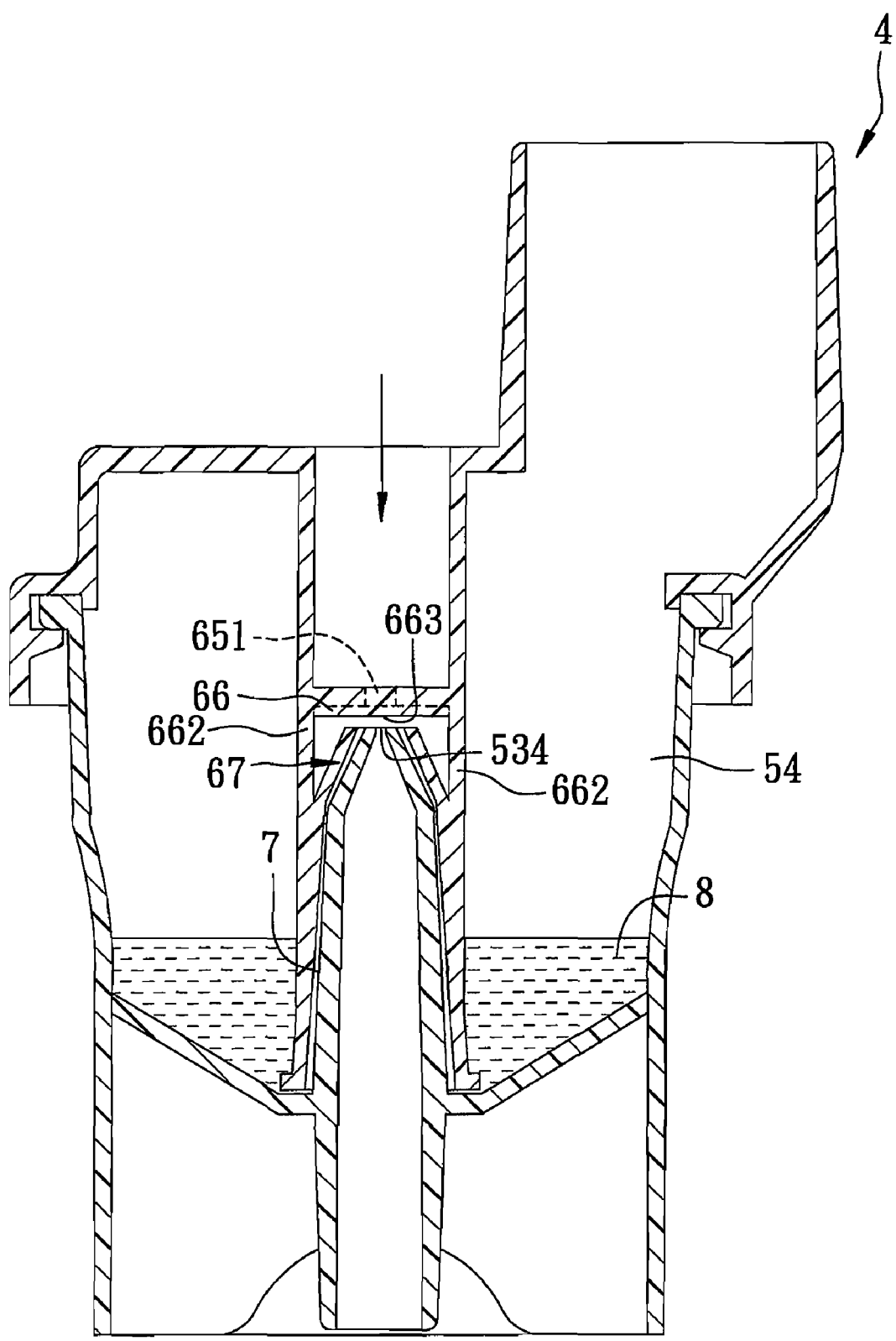
FIG. 5 is a cross-sectional view of the preferred embodiment taken along line V-V in FIG. 3.

Referring to FIGS. 3, 4, and 5, the preferred embodiment of an atomizer 4 according to the present invention is shown to include: an enclosed reservoir defining an inner space 54 adapted to receive a liquid 8 (e.g., a liquid drug) therein; a jet nozzle 53 provided in the inner space 54 for passage of an air jet therethrough; a jacket 67 sleeved around the jet nozzle 53 to define a fluid-introducing gap 7 therebetween; an air inlet conduit 64 extending into the inner space 54, and disposed above and connected to the jacket 67; and a mist-discharging conduit 62.

Specifically, the enclosed reservoir includes a container 5 and a cap 6 connected detachably and securely to the container 5. The container 5 includes a surrounding wall 51 and a partition wall 52 extending from the surrounding wall 51 to the jet nozzle 53 and confining a bottom side of the inner space 54. The surrounding wall 51 is formed with a plurality of engaging flanges 511, each of which extends radially and outwardly from a top periphery of the surrounding wall 51.

The cap 6 includes a cover plate 61 and is formed with a plurality of engaging parts 63 on an inner side of a periphery of the cover plate 61. The engaging parts 63 of the cap 6 engage the engaging flanges 511 of the surrounding wall 51 of the container 5, respectively, so as to secure the cap 6 to the container 5.

The jet nozzle 53 extends sealingly in a jet-ejecting direction (X) through the partition wall 52 and into the inner space 54. The jet nozzle 53 includes an air inlet 533 and a tapered air outlet 534.

The air inlet conduit 64 is aligned with the jacket 67 in the jet-ejecting direction (X), and has a peripheral wall 68 extending from the cover plate 61 toward the jet nozzle 53, and a bottom wall 65 extending transversely from a periphery of the peripheral wall 68. The bottom wall 65 includes a protruded jet-blocking portion 66, and is formed with a plurality of through-holes 651. Two connecting members 662 are spaced apart from each other and interconnect the air inlet conduit 64 and the jacket 67. The jet-blocking portion 66 is aligned with and is disposed adjacent to the air outlet 534 of the jet nozzle 53 in the jet-ejecting direction (X) so as to permit the air jet from the air outlet 534 of the jet nozzle 53 and the liquid flow from the fluid-introducing gap 7 to impinge a surface 663 of the jet-blocking portion 66, thereby producing the mist of the liquid in a mist forming zone $S_2$ between the jet-blocking portion 66 and the air outlet 534 of the jet nozzle 53. The through-holes 651 are disposed around the jet-blocking portion 66, and open in the jet-ejecting direction (X) such that the mist thus produced can be accelerated to flow toward the mist-discharging conduit 62 through the assistance of the external air flowing into the mist forming zone $S_2$ through